US005866137A

United States Patent [19]
Rovinski et al.

[11] Patent Number: 5,866,137
[45] Date of Patent: Feb. 2, 1999

[54] SELF-ASSEMBLED, NON-INFECTIOUS, NON-REPLICATING; IMMUNOGENIC RETROVIRUS-LIKE PARTICLES COMPRISING MODIFIED HIV GENOMES DEVOID OF LONG TERMINAL REPEATS AND CHIMERIC ENVELOPE GLYCOPROTEINS

[75] Inventors: Benjamin Rovinski, 70 Winding Lane, Thornhill, Ontario, Canada, L4J 5H6; Joel Haynes, Middleton, Wis.; Shi Xian Cao, Toronto; Michel Henri Klein, Willowdale, both of Canada

[73] Assignee: Benjamin Rovinski

[21] Appl. No.: 453,745

[22] Filed: May 30, 1995

Related U.S. Application Data

[60] Division of Ser. No. 73,526, Jun. 9, 1993, abandoned, which is a continuation-in-part of Ser. No. 839,751, Oct. 12, 1990, Pat. No. 5,439,809.

[51] Int. Cl.$^6$ ............................ A61K 39/12; A61K 39/21; C12N 7/00; C12N 7/01
[52] U.S. Cl. ...................................... 424/199.1; 424/182.1; 424/188.1; 424/202.1; 424/208.1; 435/235.1; 435/320.1
[58] Field of Search ..................................... 435/236, 239, 435/172.3; 424/187.1, 188.1, 207.1, 208.1

[56] References Cited

FOREIGN PATENT DOCUMENTS 0272858 of 1988 European Pat. Off.
15820 of 1990 WIPO.

OTHER PUBLICATIONS

Rovinski et al., 1992, J. Virol. 66:4003–4012.
Reeck et al., 1987, Cell 50:667.
Lewin, 1987, Science 237:1570.
Haynes et al., 1991, AIDS Res. Human Retro. 7:17–27
Ohno et al., 1991, Proc. Natl. Acad. Sci. USA 88:10726–10729.
Ivanoff et al., 1991, AIDS Res. Human Retro. 7:595–603.
Haseltine, W.A., "Replication and Pathogenesis of the AIDS Virus", 1988, Jour. of Acq. Immun. Def. Synd., 1:217–240
Varmus, H. Retroviruses, 1988, Science 240:1427–1435.
Aldovini, A, and R. Young, 1990. Mutations of RNA and protein sequences involved in human immunodeficiency virus type 1 packaging result in production of noninfectious virus. J. Virol. 64:1920–1926.
Allan, J.S. et al. 1985. Major Glycoprotein antigens that induce antibodies in AIDS patients are encoded by HTLV–III. Science 228:1091–1094.
Arthur, L.O. et al, 1989. Challenge of chimpanzees (*Pantroglodytes*) immunized with human immunodeficiency virus envelope glycoprotein gp120. J. Virol. 63:5046–5053.
Arthur, L.O. et al, 1987. Serological responses in chimpanzees inoculated with human immunodeficiency virus glycoprotein (gp120) subunit vaccine. Proc. Natl. Acad. Sci. USA 84:8583–8587.
Barre–Sinoussi, F. et al; 1983. Isolation of a T–lymphocyte retrovirus from a patient at risk for acquired immune deficiency syndrome (AIDS). Science 230:868–871.
Berman, P.W., et al, 1990. Protection of chimpanzees from infection by HIV–1 after vaccination with recombinant glycoprotein gp120 but not gp160. Nature (London) 345:622–625.
Bolognesi, D.P. 1989. HIV antibodies and vaccine design AIDS 3 (suppl. 1):S111–S118.
Chanh, T.C. et al, 1986. Induction of anti–HIV neutralizing antibodies by synthetic peptides. EMBO J.5:3065–3071.
Cordonnier, A. et al., 1989. Effects of mutations in hyperconserved regions of the extracellular glycoprotein of human immunodeficiency virus type 1 on receptor binding. J. Virol. 63:4464–4468.
Dalgleish, A.G. et al, 1984. The CD4 (T4) antigen is an essential component of the receptor for the AIDS retrovirus. Nature (London) 312:763–766.
Desrosiers, R.C., et al, 1989. Vaccine protection against simian immunodificiency virus infection. Proc. Natl. Acad. Sci. USA 86:6353–6357.
DiMarzo–Veronese, F., et al, 1985. Characterization of gp41 as the transmembrane protein coded by the HTLV–III/LAV envelope gene. Science 229:1402–1405.
Dowbenko, D., et al, 1988. Epitope mapping of the human immunodeficiency virus type 1 gp120 with monoclonal antibodies. J. Virol.62.4703–4711.
Durda, P.J. et al, 1990. HIV–1 neutralizing monoclonal antibodies induced by a synthetic peptide. AIDS Res. Hum. Retroviruses 6:1115–1123.

(List continued on next page.)

*Primary Examiner*—Laurie Scheiner
*Assistant Examiner*—Jeffrey S. Parkin
*Attorney, Agent, or Firm*—Sim & McBurney

[57] ABSTRACT

This invention is directed toward self-assembled, non-infectious, non-replicating, immunogenic retrovirus-like particles comprising modified HIV-1 genomes devoid of long terminal repeats and containing nucleotide sequences encoding chimeric envelope glycoproteins. Retrovirus-like particles containing chimeric envelope glycoproteins were expressed in mammalian cells by using inducible promoters. One preferred embodiment discloses the engineering of a series of expression vectors in which a synthetic oligomer encoding gp120 residues 306 to 328 (amino acids YNKRKRIHIGP GRAFYTTKNIIG) from the V3 loop of the MN viral isolate was inserted at various positions within the endogenous HIV-1$_{LAI}$ env gene. Expression studies revealed that insertion of the heterologous V3(MN) loop segment resulted in the secretion of fully assembled HIV-like particles containing chimeric LAI/MN envelope glycoproteins. Both V3 loop epitopes were recognized by loop-specific neutralizing antibodies. Immunization with HIV-like particles containing chimeric envelope proteins induced specific antibody responses against both the autologous and heterologous V3 loop epitopes, including cross-neutralizing antibodies against the HIV-1$_{LAI}$ and HIV-1$_{MN}$ isolates.

10 Claims, 2 Drawing Sheets

OTHER PUBLICATIONS

Earl, P.L. et al. 1991. Biological and immunological properties of human immunodeficiency virus type 1 envelope glycoprotein: analysis of proteins with truncations and deletions expressedby recombinant vaccinia viruses. J. Virol. 65:31–41.

Earl, P.L. et al, 1989. Isolate–and group–specific immune responses to the envelope protein of human immunodeficiency virus induced by a live recombinant vaccinia virus in macaques. AIDS Res. Hu. Retroviruses 5:23–32.

Gallo, R.C., et al. 1984. Frequent detection and isolation of cytopathic 9HTVL–III) from patients with AIDS and at risk for AIDS. Science 224:500–503.

Gardner, M.V. 1990. Vaccination against SIV infection and disease. AIDS Res. and Hum. Retroviruses 6:835–846.

Gheyson, D., et al, 1989. Assembly and release of HIV–1 precursor pr55gag virus–like particles from recombinant baculovirius–infected cells. Cell 59:103–112.

Gibbs, C.J. et al 1991. Observations after human immunodeficiency virus immunization and challenge of human immunodeficiency virus seropositive and seronegative chimpanzees. Proc. Natl. Acad. Sci. USA 88:3348–3352.

Girard, M., et al. 1991. Immunization of chimpanzees confers protection against challenge with human immunodeficiency virus. Proc. Natl. Acad. Sci. USA 88:542–546.

Gorny, M.K. et al. 1991. Production of site–selected neutralizing human monoclonal antibodies against the third variable domain of the human immunodeficiency virus type 1 envelope glycoprotein. Proc. Natl. Acad. Sci. USA 88:3238–3242.

Goudsmit, J. et al. 1988. Human immunodeficiency virus type 1 neutralization epitope with conserved architecture elicits early type–specific antibodies in experimentally infected chimpanzees. Proc. Natl. Acad. Sci. USA 85:4478–4482.

Haffar, O.K., et al 1991. HIV–specific humoral and cellular immunity in rabbits vaccinated with recombinant human immunodeficiency virus–like gag–env particles. Virology. 183:487–495.

Haffar, O., 1990. Human Immunodeficiency virus–like, non–replicating, gag–env particles assemble in a recombinant vaccinia virus expression system. J. Virol. 64:2653–2659.

Haigwood, N.L., et al, 1992. Native but not denatured recombinant human immunodeficiency virus type 1 gp120 generates broad–spectrum neutralizing antibodies in baboons. J. Virol. 66:172–182.

Haynes, J.R., et al 1991. Production of immunogenic HIV–1 virus–like particles in stably engineered monkey cell lines. AIDS Res. Hum. Retroviruses 7:17–27.

Helseth, E, et al. 1991. Human immunodeficiency virus type 1 gp120 envelope glycoprotein regions important for association with the gp41 transmembrane glycoprotein J. Virol. 65:2119–2123.

Ho, D.D., et al, 1988. Second conserved domain of gp120 is important for HIV infectivity and antibody neutralization. Science 239:1021–1023.

Hu, S.L. et al, 1991. Neutralizing antibodies against HIV–1 BRU and SF2 isolates generated in mice immunized with recombinant vaccinia virus expressing HIV–1 (BRU) envelope glycoproteins and boosted with homologous gp160. AIDS Res. Hum. Retroviruses. 7:615–620.

Jahaverian, K. et al, 1990. Broadly neutralizing antibodies elicited by the hypervariable neutralizing determinant of HIV–1. Science 250:1590–1593.

Karacostas, V., et al 1989. Human Immunodeficiency virus–like particles produced by a vaccinia virus expression vector. Proc. Natl. Acad. Sci. USA 86:8964–8967.

Kennedy, R.C., et al, 1988. Perspectives on developing anti–idiotype–based vaccines for controlling HIV infection. AIDS 2(Suppl. 1):S119–S127.

Klatzman, D., et al 1984. T–lmphocyte T4 molecule behaves as the receptor for human retrovirus LAV. Nature (London) 312:767–768.

Kowalski, M, et al 1987. Functional regions of the envelope glycoprotein of human immunodeficiency virus type 1. Science 237:1351–1355.

Laemmli, U.K. 1970. Cleavage of structural proteins during the assembly of the head of bacteriophage T4. Nature (London) 227:680–685.

Lasky, L.A., et al, 1987. Delineation of a region of the human immunodeficiency virus type 1 gp120 glycoprotein critical for interaction with the CD4 receptor. Cell 50:975–985.

Lever, A. et al. 1989. Identification of a sequence required for efficient packaging of human immunodeficiency virus type 1 RNA into virions. J. Virol. 63:4085–4087.

Lifson, J.D. et al, 1986. Induction of CD4–dependent cell fusion by the HTLV–III/LAV envelope glycoprotein. Nature (London) 323:725–728.

Maddon, P.J. et al 1986. The T4 gene encodes the AIDS virus receptor and is expressed in the immune system and the brain. Cell 47:333–348.

Matsushita, S. et al, 1988. Characterization of a human immunodeficiency virus neutralizing monoclonal antibody and mapping of the neutralizing epitope. J. Virol. 62:2107–2114.

McCune, J.M. et al, 1988. Endoproteolytic cleavage of gp160 is required for the activation of human immunodeficiency virus. Cell 53:55–67.

Murphey–Corb, M., et al, 1991. Efficiency of SIV–DeltaB670 glycoprotein–enriched and glycoprotein–depleted subunit vaccines in protecting against infection and disease in rhesus monkeys. AIDS 5:655–662.

Murphey–Corb, M. et al, 1989. A formalin–inactivated whole SIV vaccine confers protection in macaques. Science 246:1293–1297.

Nara, P.L. et al, 1988. Purified envelope glycoproteins from human immunodeficiency virus type 1 variants induce individual, type–specific neutralizing antibodies. J. Virol 62:2622–2628.

Olshevsky, U., et al, 1990. Identification of individual human immunodeficiency virus type 1 gp120 amino acids important for CD4 receptor binding. J. Virol. 64:5701–5707.

Palker, T.J., et al, 1988. Type–specific neutralization of the human immunodeficiency virus with antibodies to env–encoded synthetic peptides. Proc. Natl. Acad. Sci. USA 85:1932–1936.

Palker, T.J., et al, 1989. Polyvalent human immunodeficiency virus synthetic immunogen comprised of envelope gp120 T helper cell sites and B cell neutralization epitopes. J. Immunol. 142:3612–3619.

Popovic, M., et al 1984. Detection, isolation, and continuous production of cytopathic retroviruses (HTLV–III) from patients with AIDS and pre–AIDS. Science 224:4979–500.

Redfield, R.R., et al 1991. A phase I evaluation of the safety and immunogenicity of vaccination with recombinant gp160 in patients with early human immunodeficiency virus infection. N. Engl. J. Med. 324:1677–1684.

Robey, W.G, et al, 1986. Prospect for prevention of human immunodeficiency virus infection: purified 120–kDa envelope glycoprotein induces neutralizing antibody. Proc. Natl. Acad. Sci. USA 83:7023–7027.

Robey, W.G., et al 1985. Characterization of envelope and core structural gene products of HTLV–III with sera from AIDS patients. Science 228:583–595.

Rovinski B.R., et al, 1992, Expression and characterization of genetically engineered human immunodeficiency virus–like particles containing modified envelope glycoproteins: implications for development of a cross–protective AIDS vaccine. J. Virol. 66:4003–4012.

Rusche, J.R., et al, 1988. Antibodies that inhibit fusion of human immunodeficiency virus–infected cells bind a 24–amino acid sequence of the viral envelope, gp120. Proc. Natl. Acad. Sci. USA 85:3198–3202.

Shafferman, A., et al 1991. Protection of macaques with a simian immunodeficiency virus envelope peptide vaccine based on conserved human immunodeficiency virus type 1 sequences. Proc. Natl. Acad. Sci. USA 88:7126–7130.

Shioda, T., et al 1990. Production of human immunodeficiency virus (HIV)–like particles from cells infected with recombinant vaccinia viruses carrying the gag gene of HIV. Virol. 175:139–148.

Skinner, M.A., et al, 1988. Neutralizing antibodies to an immunodominant envelope sequence do not prevent gp120 binding to CD4. J. Virol. 62:4195:4200.

Smith, A.J., et al, 1990. Human immunodeficiency virus type 1 Pr55$^{gag}$ and Pr160$^{gag-pol}$ expressed from a simian virus 40 late replacement vector are efficiently processed and assembled into virus–like particles. J. Virol. 64:2743–2750.

Sutjipto, S., et al 1990. Inactivated simian immunodeficiency virus vaccine failed to protect rhesus macaques from intravenous or genital mucosal infection but delayed disease in intravenously exposed animals. J. Virol. 64:2290–229.

Syu, W–Jr., et al 1990. The N–terminal region of the human immunodeficiency virus envelope glycoprotein gp120 contains potential binding sites for CD4. Proc. Natl. Acad. Sci. USA 87:3695–3699.

Towbin, H., et al, 1979. Electrophoretic transfer of proteins from polyacrylamide gets to nitrocellulose sheets: procedure and some applications. Proc. Natl. Acad. Sci. USA 76:4350–4354.

Tschachier, E., et al, 1990. Functional contribution of cysteine residues to the human immunodeficiency virus type 1 envelope. J. Virol. 64:2250–2259.

Van Eendenburg. J.P., et al 1989. Cell–mediated immune proliferative responses to HIV–1 of chimpanzees vaccinated with different vaccinia recombinant viruses. AIDS Res. Hum. Retroviruses 5:41–50.

Vzorov, A.N., et al, 1991. Highly immunogenic human immunodeficiency virus–like particles are produced by recombinant vaccinia virus–infected cells. AIDS Res. Hum. Retroviruses 7:29–36.

Willey, R.L., et al, 1988. Biosynthesis, cleavage, and degradation of the human immunodeficiency virus 1 envelope glycoprotein gp160. Proc. Natl. Acad. Sci. USA 85:9580–9584.

Zagury, D., et al, 1988. A group–specific anamnestic immune reaction agianst HIV–1 induced by a candidate vaccine against AIDS. Nature (London) 332:728–731.

Zarling, J.M., et al, 1987. Proliferative and cytotoxic T cells to AIDS virus glycoproteins in chimpanzees immunized with a recombinant vaccinia virus expressing AIDS virus envelope glycoproteins. J. Immunol. 139:988–990.

Thomas J. Palker et al The Journal of Immunology, vol. 142, No. 3, Feb. 1, 1989.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear     ( x i ) SEQUENCE DESCRIPTION: SEQ ID NO:1:

Tyr Asn Lys Arg Lys Arg Ile His Ile Gly Pro Gly Arg Ala Phe Tyr
1               5                   10                  15

Thr Thr Lys Asn Ile Ile Gly
            20

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear     ( x i ) SEQUENCE DESCRIPTION: SEQ ID NO:2:

Leu Leu Pro His Ser Asn Leu Asp His Ile Leu Glu Pro Ser Ile Pro
1               5                   10                  15

Trp Lys Ser Lys

20

(2) INFORMATION FOR SEQ ID NO:3:

(i) SEQUENCE CHARACTERISTICS:
        (A) LENGTH: 22 amino acids
        (B) TYPE: amino acid
        (C) STRANDEDNESS: single
        (D) TOPOLOGY: linear     (xi) SEQUENCE DESCRIPTION: SEQ ID NO:3:

```
Pro His Trp Thr Lys Lys Pro Asn Arg Asn Gly Gly Gly Tyr Tyr Ser
 1               5                  10                 15
Ala Ser Tyr Ser Asp Pro
             20
```

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear     (xi) SEQUENCE DESCRIPTION: SEQ ID NO:4:

```
Asn Thr Arg Lys Arg Ile Arg Ile Gln Arg Gly Pro Gly Arg Ala Phe
 1               5                  10                 15
Val Thr Ile Gly Lys
             20
```

(2) INFORMATION FOR SEQ ID NO:5:

(i) SEQUENCE CHARACTERISTICS:
        (A) LENGTH: 19 amino acids
        (B) TYPE: amino acid
        (C) STRANDEDNESS: single
        (D) TOPOLOGY: linear     (xi) SEQUENCE DESCRIPTION: SEQ ID NO:5:

```
Asn Lys Arg Lys Arg Ile His Ile Gly Pro Gly Arg Ala Phe Tyr Thr
 1               5                  10                 15
Thr Lys Asn
```

(2) INFORMATION FOR SEQ ID NO:6:

(i) SEQUENCE CHARACTERISTICS:
        (A) LENGTH: 21 amino acids
        (B) TYPE: amino acid
        (C) STRANDEDNESS: single
        (D) TOPOLOGY: linear     (xi) SEQUENCE DESCRIPTION: SEQ ID NO:6:

```
Asn Thr Arg Gln Arg Thr Pro Ile Gly Leu Gly Gln Ser Leu Tyr Thr
 1               5                  10                 15
Thr Arg Ser Arg Ser
             20
```

(2) INFORMATION FOR SEQ ID NO:7:

(i) SEQUENCE CHARACTERISTICS:
        (A) LENGTH: 29 amino acids
        (B) TYPE: amino acid
        (C) STRANDEDNESS: single
        (D) TOPOLOGY: linear     (xi) SEQUENCE DESCRIPTION: SEQ ID NO:7:

-continued

```
Ser Arg Thr Ala Tyr Asn Lys Arg Lys Arg Ile His Ile Gly Pro Gly
1               5                   10                      15

Arg Ala Phe Tyr Thr Thr Lys Asn Ile Ile Gly Thr Arg
                20              25
```

SELF-ASSEMBLED, NON-INFECTIOUS, NON-REPLICATING; IMMUNOGENIC RETROVIRUS-LIKE PARTICLES COMPRISING MODIFIED HIV GENOMES DEVOID OF LONG TERMINAL REPEATS AND CHIMERIC ENVELOPE GLYCOPROTEINS

REFERENCE TO RELATED APPLICATION

This application is a divisional of U.S. patent application Ser. No. 08/073,526 filed Jun. 9, 1993, now abandoned which itself is a continuation-in-part of U.S. patent application Ser. No. 839,751 filed Oct. 12, 1990 (now U.S. Pat. No. 5,439,809), the disclosure of which is incorporated herein by reference.

FIELD OF INVENTION

The present invention relates to the field of immunology and specifically to the preparation of retrovirus-like particles, specifically HIV-like particles, which are immunogenic and non-infectious.

BACKGROUND TO THE INVENTION

The etiologic agent of acquired immune deficiency syndrome (AIDS) is a human retrovirus termed human immunodeficiency virus (HIV) of which there are presently two major subgroups, HIV-1 and HIV-2. These viruses are responsible for an ever widening world-wide epidemic of immune deficiency and central nervous system (CNS) disorders characterized by a slow, yet progressive, degeneration of immune and CNS functions.

The earliest symptoms of HIV infection include an acute influenza-like syndrome which persists for 2 to 3 weeks. Several weeks to many months or years following infection, lymphadenopathy and/or progressive depletion in $CD4^+$ T-helper lymphocytes becomes apparent and disease evolves to the point where immune deficiency becomes manifest. The diagnosis of HIV infection is confirmed by laboratory tests which include the detection of HIV-specific antibodies and/or HIV antigens in patient sera, and the isolation of infectious virus from patient body fluids or cells. A similar disease is observed in rhesus macaques infected with the simian immunodeficiency virus (SIV).

Immune deficiency in HIV infection is characterized by opportunistic infections with microbial agents which are not normally associated with disease in otherwise healthy individuals. The severity of these infections is exacerbated by the loss of helper T-cell function, which, when combined with other symptoms, such as diarrhoea and weight loss, leads to a general wasting syndrome. Death usually results from one or more opportunistic infections. As mentioned above, CNS involvement is another manifestation of AIDS and can be the result of direct HIV-induced neurological disease as well as that of opportunistic infections.

The predominant host cells for HIV in infected individuals are the $CD4^+$ T-helper cell and the cells of the monocyte/macrophage lineage. However, increasing evidence points to the fact that HIV can infect a wide variety of cell types, $CD4^+$ and $CD4^-$ both in vivo and in vitro. These cell types include those of the haematopoietic system, the central nervous system, the gastrointestinal tract, and skin. This wide host cell tropism most likely accounts for the plethora of symptoms and the severity of disease associated with HIV infection.

HIV-1 and 2 have been the subject of massive and unprecedented research efforts in recent years in a number of areas including vaccine strategies. The development of an efficacious vaccine for prevention of HIV infection, is of considerable importance as it can be easily recognized that prevention of infection is the best way to combat any infectious disease.

Various strategies are currently being used in attempts to develop an effective vaccine against AIDS. Current strategies to develop a safe and efficacious AIDS vaccine include whole inactivated viruses, subunit vaccines, recombinant viruses, genetically engineered virus-like particles, synthetic peptides, and anti-idiotypic antibodies.

Inactivated, whole-virus vaccines consist of a purified preparation of intact particles from a given viral pathogen which has been rendered non-infectious by chemical or physical means. The inherent advantages of these vaccines are their relative ease of production and the fact that all or most of the important immunological epitopes of the virus are present. However, a major disadvantage of these vaccines is that infectious virus must be propagated on a large scale, thereby exposing production workers to significant risks, depending on the nature of the pathogen. Equally important is the fact that the virus must be rendered completely non-infectious. This poses ethical problems since it is extremely difficult to demonstrate that all infectious genetic material has been removed. Moreover, extensive inactivation regimes to kill all infectious viruses are likely to destroy or alter various immunological epitopes, thereby compromising the immunogenicity of the vaccine.

A subunit HIV vaccine consists of one or more purified HIV immunogens, either obtained from disrupted whole virus or produced in genetically engineered eukaryotic or bacterial expression systems. An important advantage of this type of vaccine is the relative ease with which these products can be produced. However, this advantage can be countered by the fact that subunit vaccines only contain a subset of HIV antigenic determinants, which in some cases can lead to a less than optimal immune response. Moreover, viral protein subunits may adopt different spatial conformations when extracted from the context of the whole-virus particle. This may affect the structure of important conformational epitopes and result in inefficient immune responses.

Live recombinant virus vaccines consist of a non-pathogenic virus, such as vaccinia or adenovirus, which has one or more non-essential genes replaced by a nucleotide sequence encoding one or more HIV antigens. Live recombinant viruses can often induce efficient immune responses to single subunits of a particular pathogenic virus. However, as with subunit vaccines, recombinant virus vaccines express only a fraction of the total antigens of a given virus which can be disadvantageous when highly efficient immune responses are required.

Future vaccines may consist of synthetic peptides containing multiple epitopes of a given pathogen. These peptides, coupled to a carrier protein and combined with an appropriate adjuvant, are potentially capable of eliciting good and lasting humoral and cellular immune responses against multiple components of a pathogen. The development of an efficacious synthetic peptide vaccine for AIDS is likely to require the full identification of all the functionally important immunological determinants of HIV-1 and HIV-2, a task which may not be completed in the very near future. An important disadvantage of peptide vaccines is the difficulty to produce synthetic molecules mimicking conformational epitopes (immunological determinants which are formed by distant amino acid residues brought together in space by protein folding). If conformational epitopes are important for protection against a particular infectious agent, it is unlikely that traditional peptide vaccine designs will prove successful.

Vaccines composed of whole, inactivated simian immunodeficiency virus (SIV) were shown either to prevent the establishment of virus infection or to delay the appearance of disease in macaques challenged with infectious virus. These encouraging results suggest that perhaps a protective immune response against HIV-1 can effectively be obtained by incorporating most of the viral antigens into a candidate vaccine.

Genetically engineered non-infectious HIV virus like particles have been expressed from mammalian and insect cells. Since such particles contain either most or all of the HIV structural antigens, they are potential candidate immunogens for the development of improved cross-protective AIDS vaccines.

Several studies have shown that the principal neutralizing determinant of HIV-1 lies within the tip of the loop forming the third variable region (V3) of gp120. Since neutralizing antibodies essentially recognize the hypervariable epitope(s) of the loop, it is conceivable to design cross-protective chimeric vaccines by inserting the V3 loop epitopes of the most predominant and divergent viral isolates into a single envelope.

Several HIV isolates have been identified and neutralizing antibodies as raised against one isolate may not neutralize the other isolates. An HIV virus like particle that expresses on its surface the V3 loop epitopes of more than one HIV isolate is desirable in an immunogen to provide an immune response against immunologically distinct HIV isolates. Additionally it may be desirable to introduce into the surface protein of the HIV virus like particle epitopes from other human retrovirus, such as HTLV-1 and HTLV-2.

SUMMARY OF INVENTION

In accordance with one aspect of the present invention, there is provided a self-assembled, non-replicating, non-infectious, retrovirus-like particle having a chimeric envelope glycoprotein, comprising a first retroviral amino acid sequence and a second retroviral amino acid sequence, wherein said first amino acid sequence is substantially homologous with the native retrovirus amino acid sequence and said second amino acid sequence is a heterologous retroviral amino acid sequence inserted into said first amino acid sequence, and wherein said retrovirus-like particle elicits an immune response to at least said heterologous amino acid sequence.

Preferably, the retrovirus-like particle elicits an immune response to both the first and second amino acid sequences. The first amino acid sequence may elicit neutralizing antibodies to the native retrovirus while the second amino acid sequence elicits neutralizing antibodies to a second retrovirus containing the heterologous retroviral amino acid sequence.

The retrovirus may be selected from HIV-1, HIV-2, HTLV-1, HTLV-2 and SIV, particularly HIV-1 or HLTV-1. The first and second amino acid sequences preferably correspond to sequences of at least one portion of retroviral surface glycoproteins.

The invention further comprises the nucleotide sequence coding for the chimeric envelope glycoprotein of the retrovirus-like particles of the invention, an expression vector capable of expressing the retrovirus-like particle in mammalian cells comprising the nucleotides sequence, immunogenic compositions capable of eliciting an immune response comprising the retrovirus-like particle of the invention or an antibody recognized thereby, and a diagnostic kit for an immunoassay comprising the retrovirus-like particle reactive to antibodies in a test sample.

The nucleotide sequence contained in the expression vector preferably is deficient in at least one sequence selected from those functionally defining long terminal repeats (LTR's), primer binding site (PBS) and a viral RNA packaging sequence, preferably all such sequences.

BRIEF DESCRIPTION OF DRAWINGS

FIGS. 1A, 1B and 1C show, in an embodiment of the present invention, constructions and Vectors to express HIV virus-like particles with modified envelope proteins. A 25-bp DNA fragment (nucleotides 753 to 777 from HIV-1$_{LAI}$) which contains viral RNA packaging sequences was deleted from plasmid pMTHIV to generate the expression vector pMTHIVd25. In this vector, transcription is driven by the human metallothionein (MT)II$_a$ promoter. Vectors pMTHIVST and pMTHIVBG were constructed by inserting synthetic oligonucleotide cassettes encoding the 23 gp120 amino acids YNKRKRIHIGPGRAFYTTKNIIG (residues 306 to 328 SEQ ID NO:1) from the V3 loop of the MN isolate into the depicted StuI and BglII restriction sites, respectively. Vectors pSP4Ad25-7 and pMTHIVSP2-4 were constructed by inserting synthetic oligonucleotide cassettes encoding the amino acids LLPHSNLDHILPSIPWKSK and PHWTKKPNRNGGGYYSASYSDP respectively, corresponding to epitopic regions of HTLV-I, at the depicted StuI restriction site. The predicted amino acid sequence of inserted epitopes is indicated for each individual construct. SD, splice donor; pA, simian virus 40 polyadenylation site; MT, MT promoter.

GENERAL DESCRIPTION OF INVENTION

Particular retrovirus-like particles which may be provided herein comprise an HIV-1 or HTLV-1 insertion within the conserved region (C2) of HIV-1 gp120. The amino acid sequence of the insert preferably comprises an epitopic sequence of a V3 loop of an HIV-1 isolate or an epitopic sequence of an HTLV-1 isolate.

Such insertion conveniently may be effected by inserting a nucleotide sequence including a sequence coding from the second amino acid sequence into a nucleotide sequence coding for the first amino acid sequence at an endogenous restriction site selected from BglII and StuI site within the nucleotide sequence coding for the C2 conserved region.

Such first amino acid sequence preferably comprises the gp120 of HIV-1 LAI isolate and the second amino acid sequence comprises an epitopic sequence of the V3 loop of HIV-1 MN isolate or an epitopic sequence of an HTLV-1 isolate.

DETAILED DESCRIPTION OF INVENTION

Figure 1A:
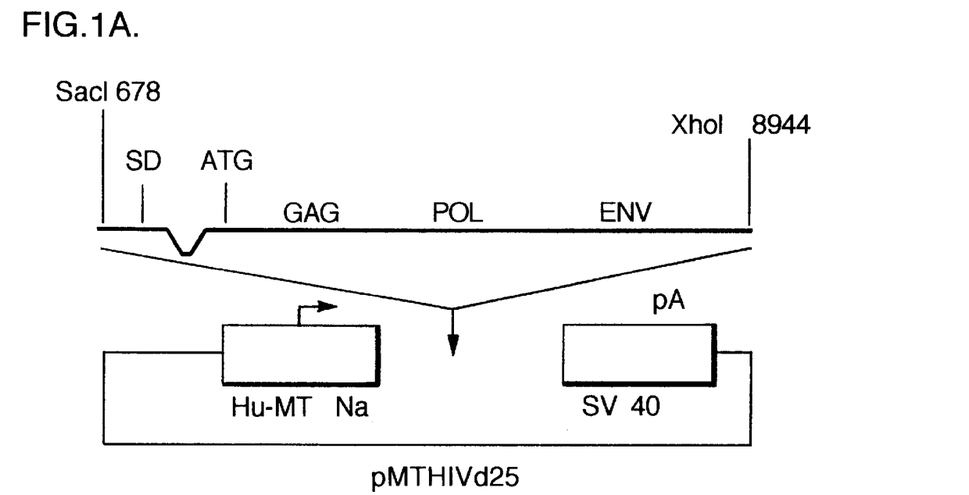
Figure 1B:
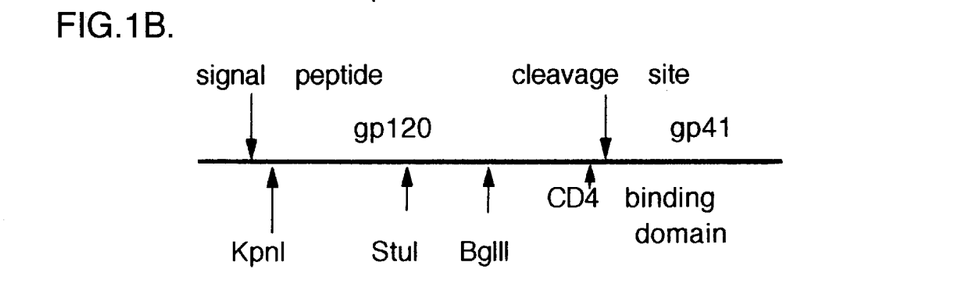
Figure 1C:
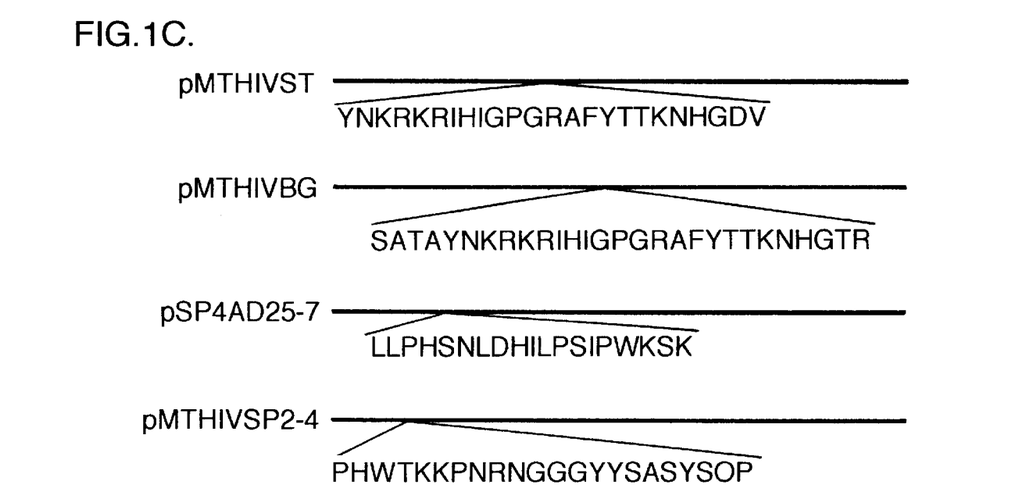

Referring to FIG. 1, there is depicted a vector for the expression of a human immunodeficiency virus-like particle containing modified envelope glycoproteins in mammalian cells, in accordance with an embodiment of the invention. The vectors include the inducible human metallothionein IIA MT promoter and the simian virus 40 polyadenylation site. An 8.3 kb SacI to XhoI DNA fragment encoding the GAG, POL and ENV proteins of HIV-LAI is under the transcriptional regulation of the Hu-MTIIA promoter.

The modifications may include deletion of nucleotides 753 to 777 to delete an RNA packaging sequence and insertion of nucleotides encoding epitopes from heterologous retroviruses, such as a neutralizing epitope from the V3 loop of the HIV-$I_{MN}$ isolate at the StuI and BglII sites of the HIV-$_{LAI}$ ENV gene, which insertion might include amino acid sequence YNKRKRIHIGPGRAFYTTKNIIG (SEQ ID NO:1). In addition, the insertion might include amino acids, corresponding to the epitopic region of HTLV-1 or HTLV-2. These sequences might include LLPHSNLDHILEPSIPWKSK (SEQ ID NO:2) or PHWTKKPNRNGGGYYSASYSDP (SEQ ID NO:3).

The plasmid, containing the modified HIV genome, can be introduced into mammalian cells, such as HeLa, COS-7 or Vero cell by transfection and transient or permanent expression of the HIV-VLPs obtained. The HIV-VLPs can be isolated from culture supernatant by, for example, by pelleting and sucrose gradient purification. The VLPs obtained can be analyzed by immunoblotting and measurement at TR activity.

The VLPs having chimeric envelope glycoproteins can be used to elicit an immune response against at least the heterologous amino acid sequence, and preferably to both the native and heterologous sequences. Preferably antibodies are generated that neutralize the native and heterologous retroviruses.

These retrovirus-like particles are useful in immunogenic compositions for eliciting an immune response against multiple retroviruses, the generation of immune sera useful in passive immunization and as a component of diagnostic kits.

BIOLOGICAL DEPOSITS

Certain biological materials are described and referred to herein that have been deposited with the American Type Culture Collection (ATCC) located at 12301 Parklawn Dr. Rockville, Md., USA, pursuant to the Budapest Treaty and prior to the filing of this application. The deposited plasmids will become available to the public upon grant of a patent based upon this United States patent application. The invention described and claimed herein is not to be limited in scope by the plasmids deposited, since the deposited embodiment is intended only as an illustration of the invention. Any equivalent plasmids that can be used to produce equivalent retrovirus-like particles as described in this application are within the scope of the invention.

The following biological deposits were made at the ATCC on Jun. 16, 1993:

| | |
|---|---|
| Plasmid DNA, pMTHIVSP2-4 | 75479 |
| Plasmid DNA, PSP4Ad25-7 | 75480 |
| Plasmid DNA, pMTHIVST | 75481 |
| Plasmid DNA, pMTHIVBG | 75482" |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Example 1

This Example describes the construction of expression vectors for the production of HIV virus like particles having natural and modified envelope proteins.

Referring to FIG. 1, the expression plasmid vector pMTHIVd25 was constructed from PMTHIV (ATCC No. 40912) by deleting a 25-bp DNA fragment (nucleotides 753 to 777; LAI sequence) containing viral RNA packaging sequences. In this vector, the transcription of the HIV-1 coding sequences is regulated by the inducible human metallothionein MT $II_a$ promoter and a simian virus 40 polyadenylation sequence. Vectors pMTHIVST and pMTHIVBG were constructed by inserting synthetic oligonucleotide cassettes encoding amino acid residues 306 to 328 from the V3(MN) loop sequence into the indicated StuI and BglII restriction sites, respectively. For all constructs, the synthetic DNA cassettes were designed to encode additional amino acid residues to maintain the reading frame and create unique restriction sites flanking the heterologous V3(MN) loop DNA segment. The nucleotide sequences of all constructs were confirmed by DNA sequencing.

Example 2

This Example describes cell culture and transfections.

Monkey COS-7 and Vero cells were grown and passaged bi-weekly in Dulbecco's modified Eagle's medium (DMEM; Flow Laboratories, McLean, Va.) supplemented with 10% heat-inactivated fetal bovine serum, glutamine (2 mM), penicillin (50 IU/ml), and streptomycin (50 ug/ml).

COS-7, HeLa and Vero cells were grown to 80% confluence and transfected with 20 µg of plasmid DNA either by Lipofectin™ (BRL; Bethesda Research Laboratories, Gaithersburg, Md.) or by the Transfinity™ (BRL) calcium phosphate procedure. Cells transfected with plasmids containing the human metallothionein promoter were induced 24–36 h after transfection with 5 µM $CdCl_2$ for 12–16 h. Cells and culture supernatants were typically analyzed for protein expression 48 h post-transfection.

Example 3

This Example describes the isolation and characterization of HIV virus like particles.

Culture media from transfected cells were collected and clarified by centrifugation at 2,000×g (Sorvall RT 6000B; Dupont Company, Wilmington, Del.) for 15 min at 4° C. Virus-like particles were isolated by ultracentrifugation as previously described.

To purify HIV-like particles for immunogenicity studies, pelleted particles obtained by ultracentrifugation of cell culture supernatants were resuspended in 200 µl of TNE buffer (10 mM Tris-HCl, pH 8.0, 100 mM NaCl, and 1 mM EDTA), overlaid onto a continuous sucrose gradient (20–60% w/v), and sedimented at 100,000×g in a Beckman SW40 rotor for 1.5 h at 4° C. The gradient fractions were collected from the bottom in 500 µl aliquots. Reverse transcriptase activity was measured in each fraction. The pellet was resuspended in 30 µl of Triton X-100 lysis buffer (50 mM Tris-HCl, 100 mM NaCl, 1 mm dithiothreitol, 0.1% Triton X-100, pH 7.8) for subsequent reverse transcriptase activity analysis. One third of the resuspended sample was added to a 90 µl reaction mixture containing 40 mM Tris-HCl, 4 mM dithiothreitol, 45 mM KCl, 10 mM $MgCl_2$, 20 µCi 3H-dTTP (80 Ci/mmol), 50 µg poly rA, and 1 µg oligo dT at pH 7.8. This mixture was incubated at 37° C. for 30 minutes. Radioactive incorporation into trichloroacetic acid-precipitable nucleic acids indicated the presence of reverse transcriptase activity.

Figure 2:
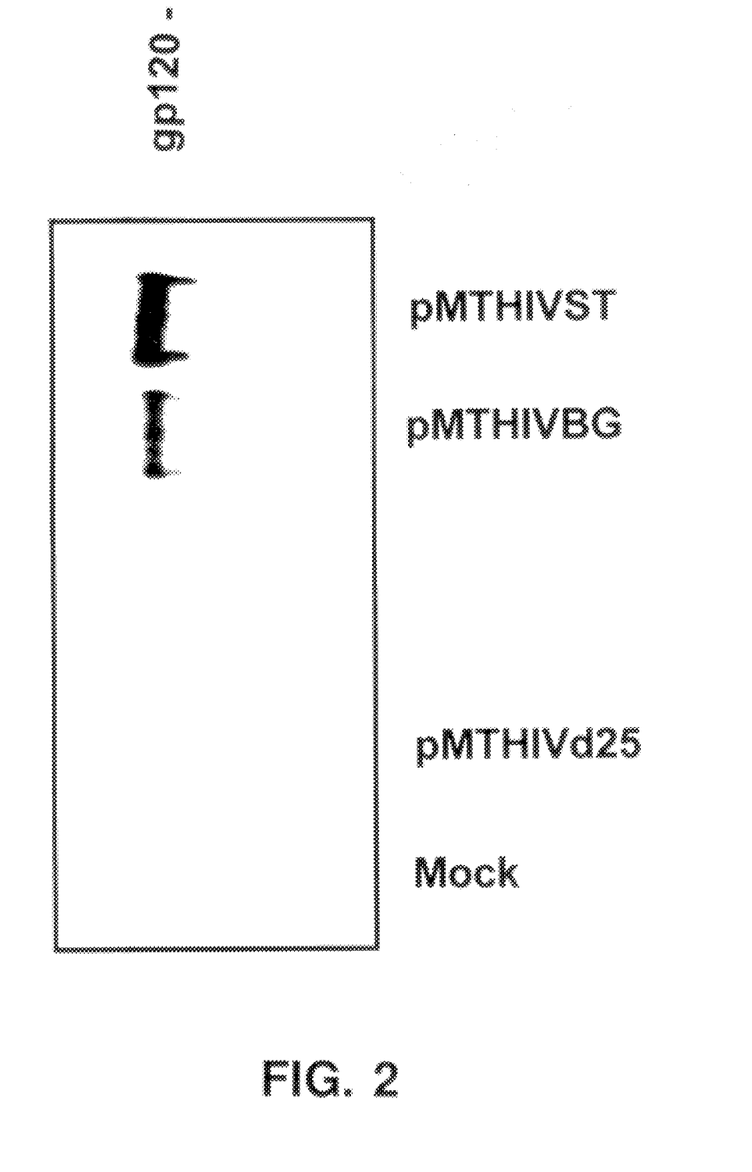
FIG. 2 shows an immunoblot analysis of material immunoprecipitated from supernatants of cells transfected with control (pMTHIVd25) and mutated (pMTHIVST and pMTHIVBG) expression vectors. Culture supernatants of cells transfected with the various recombinant plasmid constructs were first immunoprecipitated in the absence of any detergent or denaturing agents with the human monoclonal antibody 268-11D which specifically recognizes a neutralization epitope within the V3 loop of an HIV-1$_{MN}$ envelope. Immunoprecipitates were then resolved by SDS-PAGE and analyzed by immunoblotting using the mouse anti-gp120 (III$_B$) monoclonal antibody 5023 (Dupont). Mock, immunoprecipitate of mock-transfected cell supernatant.

To establish that the gp120 subunits produced by pMTHIVST and pMTHIVBG contained the heterologous V3(MN) loop epitope(s), the envelope proteins were immunoprecipitated in the absence of any detergents or denaturing agents with the human monoclonal antibody 268-11D directed against a neutralization epitope of the V3(MN)

loop. Immunoprecipitates were then resolved by SDS-PAGE and analyzed by immunoblotting with the mouse anti-gp120 (III$_B$) monoclonal antibody 5023. The immunoblot analysis (FIG. 2) revealed that antibody 5023 specifically recognized a single band corresponding to gp120 in immunoprecipitates from the supernatants of cells transfected with the pMTHIVST and pMTHIVBG constructs. These results clearly indicate that the processed ENV glycoprotein expressed from these vectors contain the heterologous V3(MN) loop segment.

Example 4

This Example describes the immunogenicity of HIV virus like particles.

Fully-assembled, envelope-containing particles were isolated from the supernatants of stably engineered Vero cells transfected with plasmids pMTHIVd25, pMTHIVST, and pMTHIVBG, by ultracentrifugation through a glycerol cushion and purified by sucrose gradient fractionation. The p24 content of the various particle species was determined by a p24-specific enzyme immunoassay (Coulter Immunology, Hialeah, Fla.). All stable cell lines secreted approximately 500 $\mu$g of p24 per liter.

Female SJL/J mice (Charles River, Montreal, Quebec) between 6 and 8 weeks of age were immunized subcutaneously with doses of purified particles corresponding to 10 $\mu$g of p24 antigen emulsified in Freund's complete adjuvant (FCA). A booster injection equivalent to 5 $\mu$g of p24 antigen was given 3 weeks later in Freund's incomplete adjuvant (FIA). Mice were sacrificed 9 days after the second immunization, and sera were collected and heat-inactivated at 56° C. for 30 minutes. The presence of antibodies to HIV-1 antigens was determined by antigen-specific enzyme-linked immunosorbent assay (ELISA). ELISA plates (LKELKAY plates; Lab Systems, Shrewsbury, Mass.) were coated at 20° C. for 18 h with 100 $\mu$l of a solution containing either gp120 or p24 at 0.1 $\mu$g/ml or peptides at 10 $\mu$g/ml in 50 mM carbonate buffer, pH 9.6. The recombinant gp120 was obtained from American Bio-Technologies, Inc. (Cambridge, Mass.), and p24 from Dupont Canada, Inc. (Markham, ON). Synthetic peptides corresponding to the neutralizing determinant found in the V3 loops of gp120 from HIV-1 strains HXB2, MN, and ELI (Table 1) were purchased from American Bio-Technologies, Inc. (Cambridge, Mass.). Plates were blocked at room temperature for 1 h with 200 $\mu$l of 2% gelatin in PBS, and washed three times with PBS containing 0.05% Tween-20. Serum samples were serially diluted in PBS/Tween-20 and added to individual wells for 1.5 h at room temperature. The plates were then washed three times with PBS/Tween-20, and a goat anti-mouse IgG-horseradish peroxidase enzyme conjugate (Amersham Canada Ltd, Oakville, ON) diluted 1:5000 in PBS/Tween-20 was added for 30 min at 37° C. After an additional washing step, the color was developed using 0.1% tetramethylbenzidine and 0.004% hydrogen peroxide (ADI Diagnostics, Willowdale, ON). Optical density was read at 450 nm using a Titertek Multiskan MCC/340 plate reader (Flow Laboratories, McLean, Va.). Endpoint titers were defined as the highest serum dilution which resulted in optical density readings at least two-fold greater than the baseline absorbance established for normal mouse serum controls.

The antibody response to envelope and core antigens to HIV virus-like particles with modified ENV proteins was analyzed by antigen-specific ELISA, and the results obtained are presented in Table 1 below.

The antisera were further tested for their reactivities with synthetic epitopes from the V3 loops of three different HIV-1 isolates. These peptides consist of amino acid residues 302–322, 307–325, and 303–323 of gp120 from the HXB2, MN, and ELI viral strains, respectively. The three expression constructs used to produce the retrovirus-like particles contain the ENV coding sequences of the HIV-$1_{LAI}$ isolate, and the reactivity of the antisera generated was tested with a peptide containing most of the V3(HXB2) loop residues but differing from the corresponding V3(LAI) sequence by only one amino acid at position 306 (Table 1). HXB2 peptide-specific titers were similar in all three groups of mice suggesting that the introduction of the heterologous V3(MN) loop segment did not affect the humoral response against the endogenous V3(LAI) loop. The particles produced by cells transfected with pMTHIVd25 that lacked the V3(MN) domain also elicited cross-reacting anti-V3(MN) antibodies (1/2500), suggesting that these antibodies recognize an epitope shared by the two V3 loop peptide sequences which are 65% similar. However, the expression vectors pMTHIVST and pMTHIVBG which contained the V3(MN) loop coding sequences produced virus-like particles which induced a markedly enhanced (1/12500) and specific antibody response against the V3(MN) loop peptide (Table 1). The lack of antibody response to the divergent V3(ELI) loop peptide served as a control for the specificity of the antibody response.

TABLE 1

Antibody responses after immunization with HIV-1 viruslike particles containing modified envelope glycoproteins

| Immunoreactivity to: | Amino acid sequence[a] 4, 5, and 6 | ELISA titer (reciprocal dilution) pMTHIVd25 | pMTHIVST | pMTHIVBG |
|---|---|---|---|---|
| Peptides | | | | |
| HXB2 | C-302NTRKRIRIQRGPGRAFVTIGK-322 | 2,500 | 2,500 | 2,500 |
| MN | C-307NKRKRIHIGPGRAFYTTKN-325 | 2,500 | 12,500 | 12,500 |
| ELI | C-303NTRQRTPIGLGQSLYTTRSRS-323 | <100 | <100 | <100 |
| Proteins | | | | |
| rpg120 | | >62,500 | >62,500 | >62,500 |
| rp24 | | >62,500 | >62,500 | >62,500 |

[a]The second and last amino acid of each peptide is numbered as to its position in the V3 loop, according to the system of Myers et al.

To determine whether immunization with HIV-like particles containing envelope proteins with the immunodominant V3 loop domains of HIV-$1_{LAI}$ and HIV-$1_{MN}$ induce neutralizing antibodies against both viral strains, guinea pigs were immunized with pMTHIVd25, pMTHIVST and pMTHIVBG. The immune sera were assayed for their ability to prevent fusion of uninfected CD4-expressing cells with cells chronically infected with either HIV-$1_{LAI}$ or HIV-$1_{MN}$. Shown are the results with serum samples obtained two weeks after the fourth booster immunization (Table 2). Animals immunized with virus-like particles containing only the V3(LAI) domain (pMTHIVd25) responded with antibodies that were effective in blocking syncytia induced by HIV-$1_{LAI}$. Immune sera from guinea pigs immunized with particles containing the V3 loop domains of HIV-$1_{LAI}$ and HIV-$1_{MN}$ (pMTHIVST and pMTHIVBG) also blocked fusion of CD4-expressing cells with cells chronically infected with HIV-$1_{LAI}$. In addition, immunization with HIV virus-like particles containing chimeric envelopes was very effective in inducing cross-neutralizing antibody responses since six of seven samples from immunized animals were able to block syncytia induced by either HIV-$1_{LAI}$ or HIV-$1_{MN}$. Cross-neutralizing activity was also observed in the serum of 1 of 3 guinea pigs immunized with virus-like particles containing only the V3(LAI) loop domain. Some of the sera were also checked for their ability to blockade HIV-$1_{RAF}$ or HIV-2Z, and none of the tested samples prevented syncytia induced by these viral strains.

TABLE 2

| | | Cell fusion blockade | |
|---|---|---|---|
| | | Fusion inhibition" | |
| Serum sample | Antigen | HIV-$1_{LA1}$ | HIV-$1_{MN}$ |
| 11 | pMTHIVd25 | + | − |
| 12 | pMTHIVd25 | − | − |
| 13 | pMTHIVd25 | + | + |
| 15 | pMTHIVST | − | + |
| 16 | pMTHIVST | + | + |
| 17 | pMTHIVST | + | + |
| 19 | pMTHIVBG | + | + |
| 20 | pMTHIVBG | − | − |
| 21 | pMTHIVBG | + | + |
| 22 | pMTHIVBG | + | + |

"Adsorbed serum samples were tested at a final dilution of 1/10 to block syncytium formation induced by CEM-cells chronically infected with either HIV-$1_{LA1}$ or HIV-$1_{MN}$. Numbers of syncytia in uninhibited wells (pre-immune or normal sera) were greater than 50 for each virus. A negative (−) score indicates no inhibition and a positive score (+) indicates fusion inhibition by the test serum, with five or less syncytia per well.

What we claim is:

1. A self-assembled, non-infectious, non-replicating, immunogenic, retrovirus-like particle encoded by a modified HIV genome devoid of long terminal repeats containing a nucleotide sequence coding for a chimeric envelope glycoprotein, said chimeric envelope glycoprotein having a first retroviral envelope amino acid sequence and a second retroviral envelope amino acid sequence, wherein said first amino acid sequence contains the HIV-1 gp120 conserved region 2 and said second amino acid sequence contains a retroviral envelope amino acid sequence of a heterologous strain of HIV-1, HIV-2, HTLV-I, or HTLV-II inserted into said first retroviral envelope amino acid sequence by inserting a nucleotide sequence encoding said second retroviral envelope amino acid sequence into a nucleotide sequence encoding said first retroviral envelope amino acid sequence at an endogenous conserved region 2 restriction site selected from the group consisting of BglII and StuI.

2. The immunogenic, retrovirus-like particle of claim 1 wherein said particle is capable of eliciting an immune response to both the first and second retroviral envelope amino acid sequences.

3. The immunogenic, retrovirus-like particle of claim 2 wherein said particle is capable of eliciting a neutralizing antibody response to both the first and second retroviral envelope amino acid sequences.

4. The immunogenic, retrovirus-like particle of claim 1 wherein said chimeric envelope glycoprotein contains an HIV-1 or HTLV-I second retroviral envelope amino acid sequence.

5. The immunogenic, retrovirus-like particle of claim 1 wherein said second amino acid sequence contains a heterologous HIV-1 V3 loop neutralizing epitope comprising the amino acids GPGR.

6. The immunogenic, retrovirus-like particle of claim 1 wherein said second amino acid sequence contains an HTLV-I gp46 neutralizing epitope.

7. The immunogenic, retrovirus-like particle of claim 1 wherein said first amino acid sequence comprises the HIV-$1_{LAI}$ gp120.

8. The immunogenic, retrovirus-like particle of claim 1 wherein said first amino acid sequence comprises the HIV-$1_{LAI}$ gp120 and said second amino acid sequence contains an HIV-$1_{MN}$ V3 loop neutralizing epitope.

9. The immunogenic, retrovirus-like particle of claim 1 wherein said second amino acid sequence has the amino acid sequence set forth in SEQ ID NO.: 1, SEQ ID NO.: 2, SEQ ID NO.: 3, or SEQ ID NO.: 7.

10. An immunogenic composition comprising the retrovirus-like particle of claim 1.

* * * * *

UNITED STATES PATENT AND TRADEMARK OFFICE
CERTIFICATE OF CORRECTION

PATENT NO.   : 5,866,137
DATED        : Feb. 2, 1999
INVENTOR(S)  : Benjamin Rovinski, et al It is certified that error appears in the above-identified patent and that said Letters Patent is hereby corrected as shown below:

On title page, item [73] should read  --Connaught Laboratories Limited--

Signed and Sealed this

Fourth Day of January, 2000

Attest:

Attesting Officer

*Acting Commissioner of Patents and Trademarks*